(12) United States Patent
Lowinger et al.

(10) Patent No.: US 7,129,210 B2
(45) Date of Patent: Oct. 31, 2006

(54) TISSUE ADHESIVE SEALANT

(75) Inventors: Johan Lowinger, Dexter, MI (US); Bruno Lowinger, Saline, MI (US); Frank DeLustro, North Charleston, SC (US); David Cox, Woodbury, MN (US); David A. Browdie, Scranton, PA (US)

(73) Assignee: Covalent Medical, Inc., Ann Arbor, MI (US)

( * ) Notice: Subject to any disclaimer, the term of this patent is extended or adjusted under 35 U.S.C. 154(b) by 0 days.

(21) Appl. No.: 10/894,609

(22) Filed: Jul. 20, 2004
(Under 37 CFR 1.47)

(65) Prior Publication Data
US 2005/0069589 A1    Mar. 31, 2005

Related U.S. Application Data

(60) Provisional application No. 60/489,438, filed on Jul. 23, 2003.

(51) Int. Cl.
*A01N 37/18* (2006.01)
*A61K 38/38* (2006.01)
*A61K 38/39* (2006.01)
*A61F 13/00* (2006.01)
*A61F 13/02* (2006.01)

(52) U.S. Cl. .................... 514/2; 530/350; 530/353; 530/354; 530/356; 530/360; 530/362; 530/363; 530/365; 530/367; 424/443

(58) Field of Classification Search ................ 435/174; 514/2, 21; 424/488; 525/54.1
See application file for complete search history.

(56) References Cited

U.S. PATENT DOCUMENTS

| 3,438,374 | A | * | 4/1969 | Falb et al. .................. 606/214 |
| 5,292,362 | A | | 3/1994 | Bass et al. |
| 5,385,606 | A | | 1/1995 | Kowanko .................... 106/124 |
| 5,445,597 | A | | 8/1995 | Clark et al. .................... 602/48 |
| 5,583,114 | A | | 12/1996 | Barrows et al. ............... 514/21 |
| 5,916,577 | A | | 6/1999 | Golz et al. .................. 424/401 |
| 6,214,331 | B1 | | 4/2001 | Vanderhoff et al. ....... 424/78.17 |
| 6,310,036 | B1 | * | 10/2001 | Browdie ........................ 514/2 |
| 2003/0104589 | A1 | * | 6/2003 | Stedronsky et al. ........ 435/174 |

OTHER PUBLICATIONS

"CryoLife, Inc.'s (CRY) BioGlue(R) Surgical Adhesive Shown to Reduce Bleeding in Ventricular Device Surgery." Feb. 3, 2003. <http://links.biospace.com/ccis/news_story.cfm?StoryID=11580320&full=1>.
"CryoLife, Inc.'s (CRY) BioGlue Shown Effective in Pituitary Tumor Surgery." Feb. 4, 2003. <http://links.biospace.com/ccis/news_story.cfm?StoryID=11603820&full=1>.
"Competitive Technologies, Inc. Obtains Exclusive Rights to Wound Sealant Technology." Jun. 2, 2003. <http://links.biospace.com/ccis/news_story.cfm?StoryID=12877620&full=1>.
Davol, Inc. Product Catalog. <http://www.davol.com/HTMLFiles/Hemostasis/HemostasisProducts1.html> (Dec. 23, 2003).
Alam, Hasan B. et al. (2003). "Comparative Analysis of Hemostatic Agents in a Swine Model of Lethal Groin Injury." Journal of Trauma 54(6):1077-1082.
Silber, Sigmund et al. (1999). "A Novel Vascular Sealing Device for Closure of Percutaneous Arterial Access Sites." America: Journal of Cardiology 83:1248-1252.
Eybl, E. et al. "Endothelial cell lining of bioprosthetic heart valve materials." The Journal of Thoracic and Cardiovascular Surgery 104: 763-769. (1992).
Sung, Hsing-Wen et al. (2003) "A natural compound (reuterin) produced by Lacrobacillus reuteri for biological-tissue fixation." Biomaterials 24:1335-1347.
Gough, Julie E. et al. "Cytotoxicity ofglutaraldehyde crosslinked collagen/poly(vinyl alcohol) films is by the mechanism of apoptosis." Journal of Biomedical Materials Research 61(1)121-130. (Jul. 2002).
Ukeda, Hiroyuki et al. (1995) "Dynamic analysis of the binding process of bovine serum albumin on glutaraldehyde activated controlled pore glass." Analytica Chimica Acta 308:261-268.
Monteiro Jr., Oyrton A.C. et al. (1999) "Some studies of crosslinking chitosan-glutaraldehyde interaction in a homogeneous system." International Journal of Biological Macromolecules 26:119-128.
Dijkstra, P.J. et al. (1996) "Chemical Stabilization of Collagen Based Biomaterials." Cardiovascular Pathology 5(5):286-295.
Greisler, Howard P. et al. "Regulation of Tissue Responses to Vascular Grafts." Cardiovascular Pathology 5(5):286-295. (1996).
"Histotechniques." The Internet Pathology Laboratory. <http://medlib.med.utah.edu/WebPath/Histhtml/Histotch/Histotch.html> (May 12, 2002).
Pusateri, Anthony E. et al. "Effect of a Chitosan-Based Hemostatic Dressing on Blood Loss and Survival in a Model of :Severe Venous Hemorrhage and Hepatic Injury in Swine." The Journal of Trauma 54(1)177-182. (2003).
Wadia, Yasmin et al. (2001) "Sutureless Liver Repair and Hemorrhage Control Using Laser-Mediated Fusion of Human Albumin as a Solder." The Journal of Trauma 51:51-59.
Vaezy, Shahram et al. (1999) "Control ofSplenicBleeding by Using High Intensity Ultrasound." The Journal of Trauma 47:521-525.

(Continued)

*Primary Examiner*—Karen Cochrane Carlson
*Assistant Examiner*—Marsha Tsay
(74) *Attorney, Agent, or Firm*—Gifford, Krass, Groh, Sprinkle, Anderson & Citkowski, P.C.

(57) ABSTRACT

A tissue adhesive sealant includes a cross-linkable protein in a solution that when combined with a cross-linking agent solution including an aldehyde and amino acid containing species reactive with the aldehyde cross-links to form a seal. The sealant is well suited for bonding tissue alone or in combination with a patch. The ratio between the aldehyde and the amino acid containing species is between 20:1 and 1:1 on an aldehyde moiety:amino acid or peptide subunit molar basis. Particularly strong seals are formed when the protein and cross-linking agent are present in a molar ratio of between 15:1 and 1:1.

68 Claims, No Drawings

OTHER PUBLICATIONS

Holcomb, John B. et al. (1999) "Effect of Dry Fibrin Sealant Dressings versus Gauze Packing on Blood Loss in Grade V Liver Injuries in Resuscitated Swine." The Journal of Trauma 46:49-57. (Jan. 1999).

Holcomb, John B. et al. (1999) "Dry Fibrin Sealant Dressings Reduce Blood Loss, Resuscitation vol., and Improve Survival in Hypothermic Coagulathic Swine with Grade V Liver Injuries."The Journal of Trauma 47:233-242. (Aug. 1999).

Sierra D. H. et al., "Modulation of mechanical properties in multiple-component tissue adhesives", J Biomed Mater Res 5; 52(3): 534-42 (Dec. 2000).

Sierra, DH et al. (1992) "A method to determine shear adhesive strength of fibrin sealants." Journal of Applied Biomaterials 3(2):147-151.

Kjaergard, HK. (2001) "Suture support: is it advantageous?" American Journal of Surgery 182(2 Suppl):15S-20S.

Siedentop, KH et al. (2001) "Safety and efficacy of currently available fibrin tissue adhesives." Am J Otolaryngol 22(4)230-235.

Jackson, MR and Alving, BM. (1999) "Fibrin sealant in preclinical and clinical studies." Curr Opin Hematol 6(6):415-419.

Spotnitz, WD et al. (1997) "The role of sutures and fibrin sealant in wound healing." Surg Clin North Am 77(3):651-669.

Shireman, PK and Greisler, HP. (1998) "Fibrin sealant in vascular surgery: a review." Journal of the Long Term Effects of Medical Implants 8(2):117-132.

Spotnitz WD. "The future of surgical tissue adhesives." Journal of the Long Term Effects of Medical Implants 8(2):81-85. (1998).

Nakagawa, T. et al., "Development of effective cross-linking method for bioactive substance—enzyme immobilization using glutaraldehyde oligomers", Chem. & Pharm. Bulletin, vol. 37, issue 9, pp. 2463-2466 (Sep. 1989).

Otani, Y. et al., "Sealing Effect of Rapidly Curable Gelatin-Poly (L-Glutamic Acid) Hydrogel Glue on Lung Air Leak", Ann. Thorac. Surg., vol. 67, pp. 922-926 (1999).

Matthew, T. L. et al., "Four Years' Experience With Fibrin Sealant in Thoracic and Cardiovascular Surgery", Ann. Thorac. Surg. 50: 40-4 (1990).

Nicholas, J. M. et al., "Successful Use of Autologous Fibrin Gel in Traumatic Bronchopleural Fistula: Case Report", The J. of Trauma, vol. 32, No. 1, (Jan. 1992).

Berguer, R. et al., "Warning: Fatal Reaction to the Use of Fibrin Glue Deep Hepatic Wounds. Case Report", The J. of Trauma, vol. 31 (1991).

Bayfield, MS and Spotnitz, WD. (1996). "Fibrin sealant in thoracic surgery. Pulmonary applications, including management of bronchopleural fistula." Chest Surg Clin N Am 6(3):567-583.

Dunn, DJ and Goa, KL. (1999) "Fibrin sealant: a review of its use in surgery and endoscopy." Drugs 58(5):863-886.

Spotnitz WD. (2001) "Commercial fibrin sealants in surgical care." American Journal of Surgery 182(2 Suppl):8S-14S.

Spotnitz WD. (1997). "New developments in the use of fibrin sealant: a surgeon's perspective." Journal of the Long Term Effects of Medical Implants 7(3-4):243-253.

Martinowitz, U and Saltz, R. (1996). "Fibrin sealant." Current Opinions in Hematology 3(5):395-402. (Sep. 1996).

Clark, RA. (2000) "Fibrin sealant in wound repair: a systematic survey of the literature." Expert Opin Investig Drugs 9(10):2371-2392. (Oct. 2000).

Radosevich, M. et al. (1997) "Fibrin sealant: scientific rationale, production methods, properties, and current clinical use." Vox Sang 72(3):133-143.

Sierra, D.H. et al. (1990) "The use of fibrin glue in intracranial procedures: preliminary results." Laryngoscope 100(4):360-363. (Apr. 1990).

Saltz, R. et al. (1991) "Experimental and clinical applications of fibrin glue." Plastic and Reconstructive Surgery 88(6):1005-1015.

Sierra, D.H. (1993). "Fibrin sealant adhesive systems: a review of their chemistry, material properties and clinical applications." J Biomater Appl 7(4):309-352. (Apr. 1993).

Wong, Kit et al. (1997) "Effects of Fibrin Glue in the Reduction of Postthoracotomy Alveolar Air Leak." Ann Thorac Surg 64:979-981.

Bachet, Jean and Daniel Guilmet. (1999) "The use of biological glue in aortic surgery." Diseases of the Aorta 17(4)779-796. (Nov. 1999).

Hewitt, Charles W. et al. (2001) "BioGlue Surgical Adhesive for Thoracic Aortic Repair During Coagulopathy: Efficacy and Histopathology." Ann Thorac Surg 71:1609-1612.

Spotnitz W.D. et al. (1997) "The Role of Sutures and Fibrin Sealant in Wound Healing." Wound Healing 77(3):651-669. (Jun. 1997).

Rousou, J. et al. (1989) "Randomized clinical trial of fibrin sealant in patients undergoing resternotomy or reoperation after cardiac operations." Journal of Thoracic and Cardiovascular Surgery 97:194-203.

"CryoLife Privately Raises $20M, Calls Near Term 'Very Promising.'" NewsEdge, Jan. 28, 2004.

Corno, Antonio F. et al. (2003) "Off-bypass implantation of a self-expandable valved stent between inferior vena cava and right atrium." Interactive Cardiovascular and Thoracic Surgery 2:166-169. (2003).

Birbaum, Yochai et al. (2002) "Ventricular Septal Rupture after Acute Myocardial Infarction." The New England Journal of Medicine 347:1426-1432. (Oct. 31, 2002).

510(k) Summary. Trade Name: Hemosorb. Jun. 28, 2002.

"Investment & Innovation in Urology." Piper Jaffray, Inc. Sep. 1994.

Brown, R. S., Jr. et al., "A Survey of Liver Transplantation from Living Adult Donors in the United States", The New England Journal of Medicine, vol. 348, pp. 818-825 (Feb. 27, 2003).

Edwards, E. B. et al., "The Effect of the vol. of Procedures at Transplantation Centers on Mortality after Liver Transplantation", The New England Journal of Medicine, vol. 341, pp. 2049-2053 (Dec. 30, 1999).

Ziegler, K. et al., "Introduction of new crosslinks into proteins", Advances in Experimental Medicine and Biology, vol. 86A, pp. 345-354 (1977).

* cited by examiner

TISSUE ADHESIVE SEALANT

RELATED APPLICATION

This application claims priority of U.S. Provisional Patent Application Ser. No. 60/489,438 filed Jul. 23, 2003, which is incorporated herein by reference.

FIELD OF THE INVENTION

The present invention generally relates to a tissue adhesive sealant capable of bonding or sealing living tissues, and in particular, relates to a two-component composition that cross-links under surgical conditions with mechanical properties that are superior to those of undamaged tissue.

BACKGROUND OF THE INVENTION

A surgeon, regardless of specialty, in the course of a procedure is concerned with the repair of damaged tissues and vessels. Restoring tissue and circulation integrity is critical in the positive outcome of a procedure regardless of whether the damage was the result of trauma or the surgical procedure itself.

The oldest method of joining damaged tissues is the use of mechanical securements such as clamps, staples or sutures. Mechanical tissue securements have proved to suffer a variety of limitations. Mechanical securements require significant skill and are slow to apply. Further, mechanical securements are ineffectual in a number of highly vascularized organs such as the liver, lung and brain. A mechanical securement also often leaks along the line of joinder and itself causes additional trauma to surrounding tissue. These characteristics of a mechanical securement further slow the surgical procedure and healing time.

The inability of mechanical securements to staunch blood loss associated with trauma has cost innumerable lives and led to research intent on overcoming the difficulties associated with the mechanical securement. These efforts have focused on the use of an adhesive or glue capable of bonding tissue surfaces together rapidly while promoting or at least not inhibiting normal healing.

A common class of tissue adhesives is fibrin-based and contains a concentrate of fibrinogen and thrombin. The fibrin adhesives are typically two-component adhesives that when mixed together react to simulate the last stages of the clot-forming cascade. The resulting clot adheres to tissue and bridges a gap therebetween until healing can occur. However, fibrin-based adhesives have met with limited success owing to low strength and the risk of infection associated with harvesting fibrin from pooled human blood. Blood-born hepatitis and HIV, along with other possible diseases, are a matter of great concern. The use of autologous plasma to prepare a fibrin sealant overcomes this difficulty, yet is time consuming and of little value in instances of direct trauma such as that inflicted in automobile accidents or gunshot wounds.

Glues based on gelatin cross-linked with an aldehyde have also met with limited success. Representative of this class of glues are gelatin-resorcinol cross-linked with formaldehyde (GRF) or glutaraldehyde (GRFG). While gelatin-based glues have been extensively studied and shown to generally be effective, these compositions have met with limited success owing to the use of hot gelatin solutions, tissue irritation associated with the aldehyde, and the criticality of handling procedures needed to obtain proper cross-linking at the joinder site.

A variety of adhesives found in nature, such as barnacle glue, appear to have excellent polymerization and mechanical properties. However, development of natural product based glues has been hampered by the ability to purify appreciable quantities of such materials, as well as persistent concerns about the triggering of an immune response by foreign glycoproteins.

Owing to the above-described limitations, considerable development effort has been directed towards finding a suitable synthetic composition operative as a tissue glue. To this end, cyanoacrylates, polyurethanes, polymethylmethacrylates, among other synthetic polymers, have been investigated as tissue glues. Each of these synthetic compositions has met with limited success owing to a variety of problems such as toxic degradation products, poor mechanical properties, cure exotherms that overheat surrounding tissue, and not being biodegradable.

Tissue welding or laser light induced tissue glue cure have also been investigated and proven only partly successful. Laser associated tissue repair has met with limited success owing to transmural thermal injury and the need for a highly skilled and well equipped surgical team.

In view of the enormous development efforts that have taken place, there are few available tissue glue compositions that meet the requirements of sufficient mechanical strength, biocompatibility and bioavailability, in addition to handling properties consistent with a variety of surgical settings. Upon consideration of these stringent requirements for a tissue glue, the cross-linking of a water soluble protein by a biocompatible aldehyde appears to be one of the few possible solutions. Illustrative of developments in this area include U.S. Pat. Nos. 5,385,606 and 6,310,036. While the adhesives disclosed in these patents afford satisfactory biocompatibility and bioabsorbability, the usage properties and mechanical strength properties of these prior art tissue adhesives are not optimal. Thus, there exists a need for a tissue adhesive sealant that is not only biocompatible, but also is a well-defined cure and affords a bond line that exceeds in strength physiological forces encountered in the course of healing.

SUMMARY OF THE INVENTION

A tissue adhesive sealant includes a cross-linkable protein in the form of a solution or suspension. A cross-linking agent solution includes an aldehyde and an amino acid containing species reactive with the aldehyde. The aldehyde and the amino acid containing species are present in a ratio between 20:1 and 1:1. The cross-linkable protein and the cross-linking agent active components are present in a ratio of between 15:1 and 1:1. Upon combining the protein solution and cross-linking agent solution and allowing sufficient time for reaction to occur therebetween, a seal is formed capable of withstanding burst pressures of greater than physiological forces encountered. A body tissue defect is sealed, the appearance of wrinkles reduced, medical implants are formed and implanted through the use of the tissue adhesive described herein.

An amino acid containing species is reacted with a multivalent aldehyde to form an oligomeric cross-linking agent. The amino acid containing species reactive with the multivalent aldehyde includes α-amino acids, β-amino acids, dipeptides, polypeptides, proteins, glycoproteins, and combinations thereof.

A commercial kit is taught that has an at least two-component syringe having a first barrel loaded with a cross-linkable protein solution and a second barrel loaded with a cross-linking agent solution comprising an aldehyde and an amino acid containing species reactive with said aldehyde, said aldehyde and said amino acid containing species being present in a ratio between 20:1 and 1:1 and said protein and said cross-linking agent are present in a ratio of between 15:1 and 1:1 together with instructions for the use thereof as a tissue adhesive sealant delivery system. The syringe may have a third barrel containing a patch material dispensable in liquid, gel, or powder form. Alternatively, the patch material is loaded in concert with the cross-linkable protein portion of a two-barrel syringe.

DETAILED DESCRIPTION OF THE PREFERRED EMBODIMENTS

The present invention forms high strength seals and coatings with tissue masses or prosthetic materials through the cross-linking of an aqueous solution soluble protein with an oligomer formed by the reaction between an aldehyde and an amino acid containing species. The present invention has utility alone, or in combination with a patch material to stop bleeding from a tissue. The present invention further has utility to form a seal or a seal with a reinforcing patch thereover. A cross-linkable protein according to the present invention is defined herein to include a protein capable of dissolving to form a solution or forming a suspension with a physiologically suitable aqueous solvent. The preferred proteins operative in the present invention are ovalbumins, serum albumins and gelatins of human or animal origin from animals illustratively including: horse, pig, cow, sheep, kangaroo, chicken, and fish. Suspension of collagen fibers is appreciated to be operative herein as a cross-linkable protein. It is appreciated that recombinant whole or truncated proteins are operative herein so long as the recombinant proteins remain cross-linkable. Recombinant human serum albumin is well known as detailed in U.S. Pat. Nos. 5,633,146; 5,986,062; 5,521,287 and 5,440,018. A recombinant protein is appreciated to lack viral, prion or bacterial contaminants associated with harvested proteins. An albumin operative herein may contain lesser amounts of other proteins such as those found in blood plasma. Human serum albumin is a particularly preferred cross-linkable protein operative in the present invention as utilized in the context of human tissue repair. It is further appreciated that ultrafiltration or other purification technique as applied to an albumin is successful in reducing the risk of immunological response or infectious agent introduction through the use of the present invention.

To form the first component of an inventive tissue adhesive sealant, a cross-linkable protein is dissolved in water or suspended in water to form a solution containing from 1 to 55 weight percent cross-linkable protein. While aqueous solution proteins are typically present from 10 to 55 total weight percent, aqueous suspension proteins are typically present from 0.3 to 9 total weight percent. Preferably, the cross-linkable protein is dissolved in an aqueous solution of physiologically acceptable buffer. Alternatively, the protein may be maintained in a dry or powder form until mixed with the cross-linking agent. Saline is an exemplary physiological buffer. Optionally, a cross-linkable protein solution includes an additive that illustratively includes an electrolyte, a thickener, an anti-microbial, a preservative, and a colorant. An electrolyte additive, if present, is typically found in an amount that ranges from 0 to 5 total weight percent and illustratively includes sodium chloride, potassium chloride and sodium phosphate. A cross-linkable protein solution thickener according to the present invention is present from 0 to 50 total weight percent. Thickeners operative in the cross-linkable protein solution illustratively include sterilized collagen particulate, implantable grade fibrous materials such as polyamides, fluoropolymers and silk. A thickener in the present invention serves to modify the handling properties of the cross-linkable protein solution as well as to modify the mechanical properties of the resulting tissue adhesive seal. Other optional additives such as an antimicrobial, preservative and a colorant are those conventional to the art and are each present in an amount that typically ranges from 0 to 3 total weight percent. Remington's Pharmaceutical Sciences, 16th Ed., 1980, Mack Publishing Co., Easton, PA and in Goodman and Gilman's The Pharmacological Basis of Therapeutics by Hardman and Limbird, 9th Ed., 1996, McGraw-Hill, New York and in The Merck Index: an encyclopedia of chemicals, drugs, and biologicals, 12th Edition, 1996, Merck & Co., Whitehouse Station, N.J. While it is appreciated that the viscosity of a cross-linkable protein solution according to the present invention is controlled through parameters that include cross-linkable protein concentration, the amount and identity of thickener, and the presence of various other additives. A cross-linkable protein solution viscosity is readily tailored to a specific task and has viscosity between that of water and 10,000 centipoise. It generally is preferred that a cross-linkable protein solution have a viscosity sufficient to prevent runnage and therefore is generally in a range of between 10 and 1,000 centipoise.

A cross-linking agent solution component that upon combination with the cross-linkable protein solution forms an inventive tissue adhesive sealant includes a multivalent aldehyde and an amino acid containing species reactive therewith. The multivalent aldehyde according to the present invention is preferably a divalent aldehyde having a molecular weight of less than 1,000 Daltons. More preferably, the multivalent aldehyde has a $C_0$–$C_{16}$ alkyl or aryl backbone intermediate between two terminal aldehyde groups. The most preferred is a $C_3$–$C_8$ linear alkyl dialdehyde. Glutaraldehyde is a particularly preferred species of linear alkyl dialdehyde. It is appreciated that the introduction of a lesser quantity of a tri- or polyaldehyde with a majority of a dialdehyde creates cross-linkages within the cross-linking agent resulting in modified solution viscosity and final tissue adhesive mechanical properties. Typically, a tri- or polyaldehyde is present at a stoichiometric molar ratio relative to a dialdehyde of 1:1000–1:30.

An amino acid containing species is reacted with a multivalent aldehyde to form an oligomeric cross-linking agent. The amino acid containing species reactive with the multivalent aldehyde includes α-amino acids, β-amino acids, dipeptides, polypeptides, proteins, glycoproteins, and combinations thereof. It is appreciated that both d- and l-conformers of a given amino acid are operative herein with the corresponding bioabsorbability associated with each conformer. It is appreciated that an amino acid containing species according to the present invention includes salts, esters and derivatized forms thereof. Additionally, where the amino acid is a β-amino acid, the resulting adhesive is comparatively resistive to bioabsorption. Derivatives to an amino acid containing species according to the present invention include solvation enhancing moieties such as hydroxyls, thiols, sulfonyls, halos; antibiotics; radioisotopes; magnetic markers, and antibodies. Particularly preferred amino acids include acidics: glutamic and aspartic acid; aliphatics: alanine, valine, leucine and isoleucine; and amides glutamine and asparagine. A most preferred amino acid containing species is shown in Formula I:

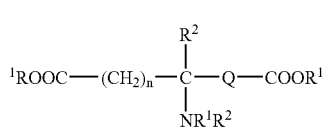

where Q is $CH_2$ or a nullity, $R^1$ is independently in each occurrence H, Na, K, $C_2$–$C_6$ alkyl; $R^2$ is independently H, $C_1$–$C_{20}$ alkyl group, a $C_0$–$C_4$ alkyl group having a substituent selected sulfonate, carboxylate, hydroxyl, quaternary amines, a radio isotopic ion, a magnetically detectable ion, an antibiotic moiety and an antibody; and n is an integer between 1 and 6 inclusive; hydrohalide salts thereof; and combinations thereof.

Preferred embodiments of the amino acid containing species of Formula I are L-glutamic acid, L-glutamic acid hydrochloride, sodium L-glutamate, potassium L-glutamate, monosodium L-glutamate, monopotassium L-glutamate, L-aspartic acid, L-aspartic acid hydrochloride, sodium L-aspartate, potassium L-aspartate, monosodium L-aspartate, and monopotassium L-aspartate, and combinations thereof. L-glutamic acid and L-aspartic acid are particularly preferred owing to the resulting cross-linking efficacy. It is appreciated that monosodium L-glutamate, L-glutamic acid hydrochloride, monopotassium L-glutamate, monosodium L-aspartate, L-aspartic acid hydrochloride, and monopotassium L-aspartate into a cross-linking solution for a longer period of time yield similarly effective cross-linking solutions relative to L-glutamic acid.

According to the present invention, the amino acid containing species is present in the cross-linking agent solution in an amount such that the molar ratio of aldehyde moieties to amino acid or peptide subunits is between 20:1 and 1:1. It is noted that within this ratio range, an increase in amino acid containing species generally tends to increase the ultimate adhesive and cohesive strengths of the cured tissue adhesive sealant. Preferably, the aldehyde moieties to amino acid or peptide subunits molar ratio is between 10:1 and 4:1. Most preferably, the ratio is between 8:1 and 6:1. In the instance where the aldehyde is glutaraldehyde and the amino acid containing species is L-glutamic acid, glutaraldehyde is typically present from 2 to 40 weight percent of the solution with the amino acid containing species being introduced in an amount to satisfy the recited ratio. As with cross-linkable protein solution, the cross-linking agent solution optionally includes pH modifiers, surfactants, antioxidants, osmotic agents and preservatives. Examples of pH modifiers include acetic acid, boric acid, hydrochloric acid, sodium acetate, sodium bisulfate, sodium borate, sodium bicarbonate, sodium citrate, sodium hydroxide, sodium nitrate, sodium phosphate, sodium sulfite, and sulfuric acid. Surfactants operative herein illustratively include benzalkonium chloride. Antioxidants operative herein illustratively include bisulfates. Electrolytes operative herein illustratively include sodium chloride. Preservatives operative herein illustratively include chlorobutanol, sorbate, benzalkonium chloride, parabens, and chlorhexadines.

The preparation of a cross-linking agent solution typically begins with the mixing of the aldehyde into water at room temperature. The pH of the resulting solution is then assured to be between 2 and 11 and preferably raised to basic with an aqueous base such as sodium hydroxide. Preferably, the pH is increased to between 8 and 11. Most preferably, pH is raised to between 8.2 and 8.8. Thereafter, sufficient solid L-glutamic acid is added to correspond to a final concentration of 0.2 molar upon full dissolution through mechanical agitation, sonication or passive dissolution. It is appreciated that variables such as the time allowed for dissolution, whether mixing occurs through agitation or sonication, the temperature of dissolution and subsequent filtering are all variables that are readily modified in the formation of a cross-linking agent solution. Proper control of these variables leads to a broad peak and high pressure liquid chromatography traces corresponding to a collection of large oligomeric species that are generally characterized in the case of glutaraldehyde-glutamic acid cross-linking agents as being hydrophilic and therefore having longer retention time on a C-18 column. This group of larger oligomeric species correlates with superior bonding properties in the cured inventive tissue adhesive sealant. Preferably, the final pH of the cross-linking solution is modified to be pH 1.5 to 9.0 prior to mixing with a cross-linkable protein solution. More preferably, the cross-linking agent solution is in a pH range of 1.5–4.5. It is appreciated that the gel time of the combined cross-linking agent solution and cross-linkable protein solution is varied as a function of cross-linking agent solution acidity. Generally, a more acidic cross-linking agent solution according to the present invention has a longer gel time than an otherwise identical cross-linking agent solution having a higher pH.

The two-component tissue adhesive composition of the present invention is applied to tissue in a number of ways. By way of illustration, the two components that make up the tissue adhesive sealant may be quickly mixed together and then applied using common applicators. A proportional sized double-barreled syringe equipped with a mixing tip is representative thereof and delivers cross-linkable protein in a molar ratio relative to the cross-linking agent of between 15:1 and 1:1. Preferably, the cross-linkable protein is delivered at a molar ratio relative to the cross-linking agent of 8:1 and 1:1. Preferably, the cross-linkable protein is delivered at a ratio relative to the cross-linking agent of 5:1 and 3:1. In actual practice, the user attaches a mixing tip to the loaded syringe and by depressing the syringe plunger a mixed pre-gelled adhesive composition is urged from the mixing tip. Alternatively, a mixing tip is replaced by a spray nozzle tip, such as that sold under the trade name TISSEEL (Immuno AG, Vienna, Austria). With a spray nozzle fitted to the double-barreled syringe, an atomized spray of ungelled adhesive composition is released upon syringe plunger depression.

An inventive tissue adhesive composition is alternatively delivered to a site of application as a three-component system including cross-linking agent, cross-linkable protein, and a patch material. Collagen is exemplary of patch materials used herein. Alternatively, transplanted or autologous tissue such as pericardial tissue may also be used. The patch material is optionally formed as a aqueous suspension that is delivered prior to, or in concert with, an inventive cross-linking agent component and a cross-linkable protein component. Simultaneous delivery of a patch material is facilitated by the use of a three-barreled syringe where the first and second barrels deliver cross-linkable protein and cross-linking agent as detailed above and the third barrel is loaded with patch material. Preferably, a mixing tip is provided with a triple-barreled syringe. Alternatively, a patch material suspension is intermixed with the cross-linkable protein component according to the present invention and delivered as a two-component system by way of a mixing or spray nozzle tip as detailed hereinabove. Optionally, a foaming agent is introduced into an inventive adhesive component to facilitate the formation of a foamed tissue adhesive. A foaming agent operative herein includes tissue compatible surfactants. Illustrative of these foaming agents are non-toxic surfactants including, but are not limited to, fats or proteins in edible foams. However, the surfactant may be an ionic or non-ionic surfactant depending on the intended application. The ionic surfactants including, for example, anionic surfactants such as sodium stearate, sodium dodecyl sulfate, α-olefinsulfonate and sulfoalkylamides and cationic surfactants such as alkyldimethylbenzylammonium salts, alkyltrimethylammonium salts and alkylpyridinium salts; and amphoteric surfactants such as imidazoline surfactants. The non-ionic surfactants including, for example, polyethylene oxide alkyl ethers, polyethylene oxide alkylphenyl ethers, glycerol fatty acid esters, sorbitan fatty acid esters, sucrose fatty acid esters, and the like.

In situations where the inventive tissue adhesive composition is delivered in conjunction with a foaming agent, preferably a propellant is provided in fluid communication with a spray nozzle tip. Propellants operative herein illustratively include aerosol propellants such as carbon dioxide, nitrogen, propane, fluorocarbons, dimethyl ether, hydrochlorofluorocarbon-22, 1-chloro-1,1-difluoroethane, 1,1-difluoroethane, and 1,1,1-trifluoro-2-fluoroethane, alone or in combination.

The tissue adhesive sealant composition of the present invention may be used in a variety of medical procedures. These include staunching arterial or venous bleeding by introducing the mixed, ungelled tissue adhesive sealant through a catheter or introducer. Alternatively, a piece of collagen is inserted into the vessel or applied on top of the vessel and coated with the mixed, ungelled inventive sealant thereby forming a seal between the outwardly facing surface of the collagen. Alternatively, hemostasis is achieved by introducing the mixed, ungelled inventive sealant to a vessel hole absent a patch material. It is appreciated that an inventive sealant can be applied from within the vessel or externally, optionally with pressure applied to the vessel hole through an inflatable catheter or external pressure. In another application, an inventive sealant composition is applied to attach skin grafts. In still another application, a patch material is secured in a holder and sequentially dip coated into the cross-linkable protein solution followed by the cross-linking agent solution, or a cross-linking and albumin solution, or spray coated with the inventive sealant mixture. The holder is then optionally used to apply pressure to a wound. Upon tissue adhesive sealant cure, the holder can then be removed. In yet another application, the patch includes two rupturable capsules or pockets respectively containing albumin and a cross-linking agent solution. The encapsulated solution is activated by breaking open the capsule (in a manner similar to known light sticks) and permitting the agents to mix prior to application of the patch. In still another application a collagen patch is delivered intrathecally or externally to an application site and then activated by applying the cross-linking agent solution. In still another application, gingival flaps are secured to dental implants, gum tissue, and/or dentin surfaces in the course of periodontal surgery. Still further indications include anastomosis and coronary artery bypass graft surgery, sealing livers following split liver resection transplants, severe bleeding in liver, spleen, lung, heart, bone, and brain tissues; sealing grafts, ruptured aorta, ruptured vena cava, torn right ventricle as a result of re-operation, dissected aorta, artificial heart valves of biological, autologous or mechanical construction, left ventricular assist devices, long-term catheters, infusion ports, and percutaneous access device ports or otherwise as an adjunct or substitute for surgical sutures or staples. Additionally, the present invention is operative in a trauma kit to seal severe bleeding at the site of injury prior to evacuation of the injured individual.

In addition to the use of an inventive tissue adhesive to seal grafts, fissures, holes, or other openings in tissue, it is appreciated that the inventive adhesive is also operative as an adjunct to conventional closure structures, sutures, staples, and clamps. As an adjunct, an inventive adhesive supplants secondary or tertiary layers of closure structures or alternatively serves as an added barrier to tissue separation. The sutures or other closure apparatus may also be pretreated or otherwise infused with albumin or collagen and subsequently glued in position by application of the cross-linking solution. It will also be appreciated that the implantation of apparatus other than closure structures (e.g., heart valve sewing cuff ring) will be enhanced by first infusing those apparatus with albumin or collagen and then applying the cross-linking solution to the apparatus after it has been implanted.

A recipient benefits from the use of an adjunct inventive tissue adhesive through reduced procedure duration and/or enhanced closure integrity. Procedures which could benefit from the present invention illustratively include the Baptista heart resection procedure, sealing livers in split liver thickness resection transplants, sealing a percutaneous access device, securing a gingival flap, stabilizing heart stent position, fixing vascular stents (or the like) inside vessels or other areas of the body, and staunching blood loss from bone.

In a dermatological context, the present invention is used topically or through subcutaneous injection to tension skin and thereby reduce the appearance of wrinkles. Scars or cheloids are similarly treated. Additionally, an inventive tissue adhesion sealant is readily injected as a filler for tissue voids alone, or in combination with a patch.

In yet another context, the present invention may be used as a bone adhesive or hard tissue repair agent or as a spinal disc replacement/filler. In this regard, calcium carbonate is added to the base sealant for use in the fixing of fractures, artificial joints or the like.

In still another application, an inventive tissue sealant is used as a binder to form various endogenous or exogenous materials into a preform medical implant. Illustrative of this application is sterilized cadaver bone implants for orthopedic bone replacement. Additionally, a soft tissue implant of collagen or other implantable material is well suited for reconstructive plastic surgery. Exogenous materials operative herein include biocompatible synthetic polymers, implantable metals, and cadaver harvested tissues; these materials in powder, gel, suspension, or solid form. By mixing the cross-linkable protein solution therewith prior to molding, and thereafter spraying with a cross-linking agent solution, a molded preform results having superior handling properties relative to conventional implants.

A "patch" is defined herein to include any shaped substrate compatible with surgical implantation and capable of being coated by an inventive sealant, shapes of which illustratively include a aqueous suspension, a solution, a powder, a paste, a sheet, a ring, a stent, a cone, a plug, a pin, a screw and complex three-dimensional shapes contoured to be complementary to specific anatomical features. Inventive patch materials illustratively include collagen; polylactic acid; hyaluronic acid; fluoropolymers; silicones; knitted or woven meshes of, for example, cellulosic fibers, polyamides, rayon acetates and titanium; skin; bone; titanium and stainless steel. Collagen is a particularly preferred patch material. Alternatively, pericardial or other body tissue may be used instead of a collagen patch. More preferably, the collagen is a flexible, fibrous sheet readily formed into a variety of shapes that is bioabsorbable and has a thickness of 2–5 millimeters. Such fibrous sheet collagen is commercially available from a number of suppliers. A collagen patch serves to enhance sealant strength while allowing some penetration of the inventive tissue sealant thereto. Optionally, in a surgical setting, a dry or a wetted absorbent gauze is placed proximal to the wound site in order to wick away any excess ungelled inventive tissue sealant prior to cure.

In addition to the holders described above, a holder of the type used for implanting an artificial heart valve may also be associated with a patch to permit a user to easily retain the patch in position. Holders of appropriate design are known in the art and include grippers for securing the valve. See also, the holders of U.S. Pat. No. 5,713,952; 5,824,068; 6,019,790 and the references cited therein. The grippers of the holder maintain the patch securely in position and are operable to release the patch once it is glued in place. Optionally, sutures (rather than a holder) may be used to hold the patch in position.

The adhesive may also be applied as a spray using, for example, the means described above or, alternatively a duel spray apparatus similar to the type disclosed by U.S. Pat. No. 4,792,062 or 6,722,532. In such an application the cross-linkable protein in a solution and a cross-linking agent solution (as discussed above) are simultaneously delivered by a spray apparatus proximate to the intended target area resulting in the mixing in air of the components as an adhesive.

The adhesive may be bondable to metals following the pretreatment of the metal with $H_2O_2$.

In the context of minimally invasive surgical procedures, illustratively including a lap-coly, another laparoscopic procedure, or the sealing leaks in a lung biopsy, the adhesive of the present invention is delivered to a target bonding site using either a tip that mixes the adhesive components prior the reaching the ends of the catheter or that delivers the glue through two separate channels and mixes it at the end. Appropriate mixing tips are described above and are known in the art.

In addition to medical treatment, the cross-linking agent solution of the adhesive has utility in preserving tissue for transplant. Specifically, a cross-linking agent solution including glutaraldehyde, as described above, may be used in the cross-linking and detoxification process for transplantation and heart valve prosthesis.

The component of the adhesive may further be infused with a pharmaceutical agent such that as the adhesive is bioabsorbed, it functions as a drug delivery agent. The pharmaceutical agents that can be delivered by the present invention include organic, inorganic and organometallic compounds without limitation. The compounds may be water soluble or water insoluble. Further, pharmaceutical agents include beneficial agents that affect a cell, tissue, organ or body system, the body system illustratively including the nervous system, cardiovascular system, immune system, reproductive system, musculoskeletal system, lymphatic system, alimentary system, excretory system, endocrine system, hormone system and blood circulatory system.

Further, pharmaceutical agents which can be included in the drug delivery system of the present invention illustratively include: an analgesic, an anesthetic, an anthelminthic, an anti-allergic, an anti-arrhythmic, an anti-asthmatic, an antibiotic, an anticonvulsant, an antidepressant, an antidiabetic, an antifungal, an antihypertensive, an anti-inflammatory agent, anti-migraine, an anti-neoplastic, an antiparasitic, an anti-tumor agent, an anti-ulcer agent, an antiviral, an anxiolytic, a bronchodilator, a cough or cold agent, a cytostatic, a hypnotic, a hypoglycemic, a metastasis inhibitor, a muscle relaxant, a neoplastic, a sedative and a tranquilizer compound. Remington's Pharmaceutical Sciences, 16th Ed., 1980, Mack Publishing Co., Easton, Pa. and in Goodman and Gilman's The Pharmacological Basis of Therapeutics by Hardman and Limbird, 9th Ed., 1996, McGraw-Hill, New York and in The Merck Index: an encyclopedia of chemicals, drugs, and biologicals, 12th Edition, 1996, Merck & Co., Whitehouse Station, N.J.

Pharmaceutical agents deliverable by the present invention are those with a molecular weight in the range from about 50 Daltons to about 10,000,000 Daltons.

Prodrugs are included in the drug delivery device of the present invention as pharmaceutical agents. The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, it is intended that the present invention include compounds made either using standard organic synthetic techniques, including combinatorial chemistry or by biological methods, such as through metabolism.

The compositions optionally include an effective amount of the selected pharmaceutical agent in combination with a pharmaceutically acceptable carrier and, in addition, may include other medicinal agents, pharmaceutical agents, carriers, or diluents. By "pharmaceutically acceptable" is meant a material that is not biologically or otherwise undesirable, which can be administered to an individual along with the selected substrate without causing significant undesirable biological effects or interacting in a deleterious manner with any of the other components of the pharmaceutical composition in which it is contained.

A single pharmaceutical agent is delivered by the drug delivery device of the present invention. Optionally, two or more pharmaceutical agents may be delivered simultaneously by the drug delivery device of the present invention.

The present invention is further illustrated by the following examples that are intended to be illustrative of particular embodiments of the present invention. These examples are not intended to limit the scope of the present invention as defined by the appended claims.

EXAMPLE 1

Preparation of Cross-linking Agent Solution

Fourteen grams of glutaraldehyde is added to 86 grams of deionized, distilled water with mechanical stirring. The resulting solution is titrated with aqueous sodium hydroxide to a pH of 8.5. Three grams of L-glutamic acid is added to the solution and allowed to mix for 72 hours until all of the added glutamic acid has dissolved.

EXAMPLE 2

Sealant Efficacy and Strength in Porcine Cardiac Injury Model

A fresh porcine heart is prepared by creating a 10–12 mm circular transmural defect in the left ventricular free wall by a sharp excision of a tissue cylinder. An 18-gauge catheter is placed through an apical 3-0 silk purse string suture into the left ventricle. The mitral valve is closed following left atriotomy with a double-layered continuous suture of 4-0 polypropylene. After dissection of the aortic root, the left ventricular outflow tract is occluded at the level of the coronary arteries with a large forceps.

A pressure-monitored water infusion system is constructed using I.V. tubing segments, an aneroid manometer, three-way stopcocks, and a balloon angioplasty pressure generator (Scimed Pressure Generator: Minneapolis, Minn.).

The left ventricular free wall defect is closed by a 3 minute application of the solution of a 40% by weight bovine serum albumin solution containing 0.375 M NaCl and the solution of Example 1 in a 4:1 ratio to the wet epicardial surface. This resulted in the formation of a circular layer of sealant overlapping the tissue defect. The left ventricle was then filled with water.

By stopcock manipulation, repeated trials of pressure-monitored, left ventricular distensions are performed while checking the site of ventricular repair for any fluid leakage. Following test termination, the portion of the left ventricular free wall surrounding the repair injury site is excised and the dimension of the repair measured with a ruler.

Repeated application of distension pressures resulted in leakage of fluid at the sites of mitral valve closure, aortic root closure, and left ventricular catheter insertion. These were then successfully sealed with liquid adhesive of the above BSA solution and Example 1. Following sealing, repeated applications of supra physiologic left ventricular distension pressures up to 2 atm is performed without leakage at the injury repair site both before and after overnight storage in 4° C. water. Testing is discontinued when escape of fluid through the left ventricular wall into subepicardial regions is observed. Inspection of the repair site showed a circular layer of sealant approximately 1 mm thick covering a 12 mm diameter circular transmural defect with an overlap length of approximately 4 mm and the repair site to be relatively flat and without obvious sealant material redundancy.

EXAMPLE 3

Effect of Cross-linkable Protein on Adhesive Strength

The process of forming the cross-linkable protein solution of above is repeated three different times. In each instance, bovine serum albumin is replaced by one of: human serum albumin, ovalbumin, and gamma globulin in like quantities. Thereafter, the process of Example 2 is repeated using each of these cross-linkable protein solutions separately as a component of the sealant according to the procedure in Example 2. Each of the sealants based on human serum albumin, ovalbumin and gamma globulin allowed for the repeated application of left ventricular distension pressures exceeding 2 atm before and after overnight storage in 4° C. water.

EXAMPLE 4

Sealant Efficacy in Porcine Liver Model

A fresh porcine liver is excised and coupled by way of the hepatic artery to a pressurized plasma solution reservoir. Other vessels were sutured and the liver pressurized to 200 torr. A 10–12 mm core is excised from the liver to simulate a gunshot. A drop in pressure and hemorrhage of plasma is noted. A collagen plug having an outer diameter of 10 mm is coated with the tissue adhesive of Example 2 and the plug inserted into the liver bore. Within 3 minutes the liver supports a coupled reservoir pressure of 150 torr. Accordingly, it will be appreciated that the adhesive of the present invention is operable to glue the collagen plug in place.

EXAMPLE 5

Sealant Efficacy in Aneurism Model

A carotid artery having an internal diameter of 4 mm is stripped from a freshly slaughtered pig. The artery is coupled at one end to a plasma reservoir and a septum added to seal the other end. The artery is pressurized to 200 torr. A 1 mm transmural circular defect is simulated by a sharp excision of a tissue cylinder. A drop in pressure and hemorrhage of plasma is noted. A 3 mm diameter collagen sheet is pushed through the artery with a catheter and lodged in the excision. The tissue adhesive of Example 2 is delivered through two separate bores in the catheter. After the sheet has been held in place for 5 minutes, the catheter is removed and the artery is again able to withstand pressurization to pre-excision values.

Any patents or publications referenced herein are hereby incorporated by reference to the same extent as if each individual reference was explicitly and individually incorporated herein by reference. These patents and publications are indicative of the level of skill in the art to which the invention pertains.

It is appreciated that one skilled in the art will note modifications and variations in the invention as described herein. These modifications and variations that are equivalent to, and within the spirit of the present invention, are intended to be encompassed within the appended claims.

The invention claimed is:

1. A tissue adhesive kit consisting:
   a cross-linkable albumin protein consisting of albumin dissolved or suspended directly in aqueous solvent to form a protein solution; and
   a cross-linking agent solution comprising an aldehyde and an amino acid containing species reactive with said aldehyde, said aldehyde and said amino acid containing species being present in a ratio between 20:1 and 1:1 applied with said protein solution to form a tissue adhesive sealant.

2. The kit of claim 1 wherein said cross-linkable protein is a recombinant protein.

3. The kit of claim 1 wherein said protein is selected from the group consisting of: serum albumin and ovalbumin.

4. The kit of claim 3 wherein said serum albumin is human serum albumin.

5. The kit of claim 3 wherein said serum albumin is bovine serum albumin.

6. The kit of claim 1 wherein said protein is water soluble and present from 10 to 55 total weight percent of said solution.

7. The kit of claim 1 wherein said protein solution further comprises a suspension of collagen fibers present from 0.3 to 9 total percent of said protein solution.

8. The kit of claim 1 wherein said cross-linking agent solution has a pH of between 1.5 and 9.

9. The kit of claim 1 wherein said aldehyde has a plurality of aldehyde moieties therein.

10. The of claim 9 wherein said aldehyde has two aldehyde moieties.

11. The kit of claim 10 further comprising a lesser amount of a second aldehyde having at least three aldehyde moieties therein.

12. The kit of claim 1 wherein said aldehyde is selected from the group consisting of: $(CH_2)_n(CHO)_2$ where n is an integer between 0 and 8, and $C_5$–$C_8$ cycloalkane dione.

13. The kit of claim 1 wherein said aldehyde is glutaraldehyde.

14. The kit of claim 1 wherein said amino acid containing species is selected from the group consisting of an amino acid, a dipeptide, a tripeptide, a polypeptide, a protein, and a glycoprotein.

15. The kit of claim 1 wherein said amino acid containing species is an amino acid having a residue selected from the group consisting of acidic, aliphatic, and amide.

16. The kit of claim 14 wherein said amino acid containing species has the formula:

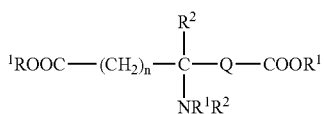

where $Q$ is $CH_2$ or a nullity; $R^1$ is independently in each occurrence H, Na, K, $C_2$–$C_6$ alkyl; $R^2$ is independently H, $C_1$–$C_{20}$ alkyl group, a $C_0$–$C_4$ alkyl group having a substituent selected sulfonate, carboxylate, hydroxyl, quaternary amines, a radioisotopic ion, a magnetically detectable ion, an antibiotic moiety and an antibody; and n is an integer between 1 and 6 inclusive; hydrohalide salts thereof; and combinations thereof.

17. The kit of claim 12 wherein said amino acid is selected from the group consisting of: L-glutamic acid and L-aspartic acid.

18. The kit of claim 1 wherein said aldehyde:amino acid containing species molar ratio is between 10:1 and 4:1.

19. The kit of claim 1 wherein said aldehyde:amino acid containing species molar ratio is between 8:1 and 6:1.

20. The kit of claim 1 further comprising a pharmaceutical agent.

21. The kit of claim 1 further comprising a patch material suspension.

22. The kit of claim 21 wherein said suspension is collagen.

23. The of claim 21 wherein said suspension is admixed with said cross-linkable protein.

24. The kit of claim 21 further comprising a foaming agent.

25. The kit of claim 24 further comprising a propellant.

26. The kit of claim 1 further comprising a patch, the patch including a first and a second rupturable capsule, the first capsule containing the cross-linkable protein and the second capsule containing the cross-linking agent solution.

27. A tissue adhesive kit consisting:
a cross-linkable protein selected from the group of casein, globulin, or gelatin consisting of said cross-linkable protein dissolved or suspended directly in aqueous solvent to form a protein solution or suspension;
a cross-linking agent solution comprising an aldehyde and an amino acid containing species reactive with said aldehyde, said aldehyde and said amino acid containing species being present in a ratio between 20:1 and 1:1.

28. The kit of claim 27 wherein said cross-linkable protein is a recombinant protein.

29. The kit of claim 27 wherein said protein suspension further comprises collagen fibers present from 0.3 to 9 total percent of said suspension.

30. The kit of claim 27 wherein said solution containing said cross-linking agent solution has a pH of between 1.5 and 9.

31. The kit of claim 27 wherein said aldehyde has a plurality of aldehyde moieties therein.

32. The kit of claim 31 wherein said aldehyde has two aldehyde moieties.

33. The kit of claim 32 further comprising a lesser amount of a second aldehyde having at least three aldehyde moieties therein.

34. The kit of claim 27 wherein said aldehyde is selected from the group consisting of: $(CH_2)_n(CHO)_2$ where n is an integer between 0 and 8, and $C_5$–$C_8$ cycloalkane dione.

35. The kit of claim 27 wherein said aldehyde is glutaraldehyde.

36. The kit of claim 27 wherein said amino acid containing species is selected from the group consisting of an amino acid, a dipeptide, a tripeptide, a polypeptide, a protein, and a glycoprotein.

37. The kit of claim 27 wherein said amino acid containing species is an amino acid having a residue selected from the group consisting of acidic, aliphatic, and amide.

38. The kit of claim 36 wherein said amino acid containing species has the formula:

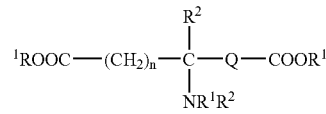

where $Q$ is $CH_2$ or a nullity; $R^1$ is independently in each occurrence H, Na, K, $C_2$–$C_6$ alkyl; $R^2$ is independently H, $C_1$–$C_{20}$ alkyl group, a $C_0$–$C_4$ alkyl group having a substituent selected sulfonate, carboxylate, hydroxyl, quaternary amines, radioisotopic ion, a magnetically detectable ion, an antibiotic moiety and an antibody; and n is an integer between 1 and 3 inclusive; hydrohalide salts thereof; and combinations thereof.

39. The kit of claim 35 wherein said amino acid is selected from the group consisting of: L-glutamic acid and L-aspartic acid.

40. The kit of claim 27 wherein said aldehyde:amino acid containing species molar ratio is between 10:1 and 4:1.

41. The kit of claim 27 wherein said aldehyde:amino acid containing species molar ratio is between 8:1 and 6:1.

42. The kit of claim 27 further comprising a pharmaceutical agent.

43. The kit of claim 27 further comprising a patch material suspension.

44. The kit of claim 43 wherein said suspension is collagen.

45. The kit of claim 43 wherein said suspension is admixed with cross-linkable protein.

46. The kit of claim 43 further comprising a foaming agent.

47. The kit of claim 43 further comprising a propellant.

48. The kit of claim 27 further comprising a patch, the patch including a first and a second rupturable capsule, the first capsule containing said cross-linkable protein and the second capsule containing the cross-linking agent solution.

49. A tissue adhesive kit consisting:
a cross-linkable suspension of collagen fiber protein consisting of collagen fiber protein suspended directly in aqueous solvent at 0.3 to 9 total weight percent to form a protein suspension; and
a cross-linking agent solution comprising an aldehyde and an amino acid containing species reactive with said aldehyde, said aldehyde and said amino acid containing species being present in a ratio between 20:1 and 1:1.

50. The kit of claim 49 wherein said cross-linkable protein is a recombinant protein.

51. The kit of claim 49 wherein said solution containing said cross-linking agent solution has a pH of between 1.5 and 9.

52. The kit of claim 49 wherein said aldehyde has a plurality of aldehyde moieties therein.

53. The kit of claim 52 wherein said aldehyde has two aldehyde moieties.

54. The kit of claim 53 further comprising a lesser amount of a second aldehyde having at least three aldehyde moieties therein.

55. The kit of claim 49 wherein said aldehyde is selected from the group consisting of: $(CH_2)_n(CHO)_2$ where n is an integer between 0 and 8, and $C_5$–$C_8$ cycloalkane dione.

56. The kit of claim 49 wherein said aldehyde is glutaraldehyde.

57. The kit of claim 49 wherein said amino acid containing species is selected from the group consisting of an amino acid, a dipeptide, a tripeptide, a polypeptide, a protein, and a glycoprotein.

58. The kit of claim 49 wherein said amino acid containing species is an amino acid having a residue selected from the group consisting of acidic, aliphatic, and amide.

59. The kit of claim 57 wherein said amino acid containing species has the formula:

$$^1ROOC-(CH_2)_n-\underset{\underset{NR^1R^2}{|}}{\overset{\overset{R^2}{|}}{C}}-Q-COOR^1$$

where Q is $CH_2$ or a nullity; $R^1$ is independently in each occurrence H, Na, K, $C_2$–$C_6$ alkyl; $R^2$ is independently H, $C_1$–$C_{20}$ alkyl group, a $C_0$–$C_4$ alkyl group having a substituent selected sulfonate, carboxylate, hydroxyl, quaternary amines, a radioisotopic ion, a magnetically detectable ion, an antibiotic moiety and an antibody; and n is an integer between 1 and 6 inclusive; hydrohalide salts thereof; and combinations thereof.

60. The kit of claim 56 wherein said amino acid is selected from the group consisting of: L-glutamic acid and L-aspartic acid.

61. The kit of claim 49 wherein said aldehyde:amino acid containing species molar ratio is between 10:1 and 4:1.

62. The kit of claim 49 further comprising a pharmaceutical agent.

63. The kit of claim 49 further comprising a patch material suspension.

64. The kit of claim 63 wherein said suspension is collagen.

65. The kit of claim 63 wherein said suspension is admixed with cross-linkable protein.

66. The kit of claim 63 further comprising a foaming agent.

67. The kit of claim 66 further comprising a propellant.

68. The kit of claim 49 further comprising a patch, the patch including a first and a second rupturable capsule, the first capsule containing the cross-linkable protein and the second capsule containing the cross-linking agent solution.

* * * * *